United States Patent [19]
Hayashi

[11] Patent Number: 5,627,612
[45] Date of Patent: May 6, 1997

[54] OPHTHALMIC APPARATUS HAVING PROGRAM STORING MEANS

[75] Inventor: Akihiro Hayashi, Toyokawa, Japan

[73] Assignee: Nidek Co. Ltd., Japan

[21] Appl. No.: 635,728

[22] Filed: Apr. 22, 1996

[30] Foreign Application Priority Data

Apr. 21, 1995 [JP] Japan .................. 7-120907

[51] Int. Cl.$^6$ .................. A61B 3/00; A61B 3/02
[52] U.S. Cl. .................. 351/200; 351/222; 351/241
[58] Field of Search .................. 351/200, 205, 351/222, 223, 227, 233, 241

[56] References Cited

U.S. PATENT DOCUMENTS

| | | | |
|---|---|---|---|
| 5,416,540 | 5/1995 | Hayashi | 351/239 |
| 5,444,504 | 8/1995 | Kobayashi | 351/237 |
| 5,490,098 | 2/1996 | Kardon | 351/200 |

FOREIGN PATENT DOCUMENTS

| | | |
|---|---|---|
| 1-62117 | 3/1989 | Japan . |
| 5-184538 | 7/1993 | Japan . |

Primary Examiner—Huy Mai
Attorney, Agent, or Firm—Rossi & Associates

[57] ABSTRACT

An ophthalmic apparatus for inspecting visual functions of eyes to be examined, providing an optical unit having ophthalmic windows, for respectively placing optical elements in the ophthalmic windows by switching, an object indicating unit for presenting an object to each eye to be examined, a display device having an operation screen for operating the object indicating unit and the optical unit, a program storing device for storing therein programs for controlling the display device, the programs having a common numeric value switching area for effecting the switching between numeric values for respective inspecting items such as a spherical degree, an astigmatic degree and an astigmatic axis, and displaying an operation screen displaying an object presented by the object indicating unit and an input screen inputting reference data for inspecting the eyes to be examined within the numeric value switching area, an input device for inputting an operation command through the use of the operation screen of the display device, and a program executing device for executing the programs in accordance with the input operation command.

10 Claims, 6 Drawing Sheets

OPHTHALMIC APPARATUS HAVING PROGRAM STORING MEANS

BACKGROUND OF THE INVENTION

1. Field of the Invention

The present invention relates to an ophthalmic apparatus for subjectively inspecting a refractive power of each eye to be examined and visual function.

2. Description of the Related Art

An ophthalmic apparatus provided with a subjective refractive power inspecting device for placing various optical elements in front of eyes to be examined is normally used to make a prescription for spectacle lenses for correcting refractive ametropia of the eyes to be examined and inspect visual function of the eyes to be examined. There has been also provided a subjective refractive power inspecting device for electromotively disposing optical elements by switching. Further, an ophthalmic apparatus has been recently provided wherein an object indicating device for presenting an object (which is also called "chart") necessary for subjective optometry is connected to a subjective refractive power inspecting device and these devices are intensively controlled by a control panel having a large number of switches. Of these apparatuses, one is also known wherein a display is provided so as to recognize optometry information.

However, the ophthalmic apparatus is accompanied by a drawback that the operation of the large number of switches while an examiner being seeing the optometry information on the display, requires much labor, so that much time is taken to find the intended switch.

Further, there was a limitation on the number of the switches placed in the control panel.

SUMMARY OF THE INVENTION

With the foregoing drawback in view, it is therefore a technical object of the present invention to provide an ophthalmic apparatus capable of performing optometry with satisfactory efficiency under easy operation of a subjective refractive power inspecting device.

According to one aspect of this invention, for achieving the above object, there is provided an ophthalmic apparatus for inspecting visual functions of eyes to be examined, comprising: an optical unit having inspection windows, for respectively placing optical elements in the inspection windows by switching; an object indicating unit for presenting an object to each eye to be examined; a display means having an operation screen for operating the object indicating unit and the optical unit; a program storing means for storing therein programs for controlling the display means, the programs having a common numeric value switching area for effecting the switching between numeric values for respective inspecting items such as a spherical degree, an astigmatic degree and an astigmatic axis, and displaying an operation screen displaying an object presented by the object indicating unit and an input screen inputting reference data for inspecting the eyes to be examined within the numeric value switching area; an input means for inputting an operation command through the use of the operation screen of the display means; and a program executing means for executing the programs in accordance with the input operation command.

According to the above constitution, optometry can be performed with satisfactory efficiency by easily operating the subjective refractive power inspecting device.

The above and other objects, features and advantages of the present invention will become apparent from the following description and the appended claims, taken in conjunction with the accompanying drawings in which a preferred embodiment of the present invention is shown by way of illustrative example.

BRIEF DESCRIPTION OF THE DRAWINGS

The present invention will be described with reference to the accompanying drawings in which.

DETAILED DESCRIPTION OF THE PREFERRED EMBODIMENTS

Figure 1:
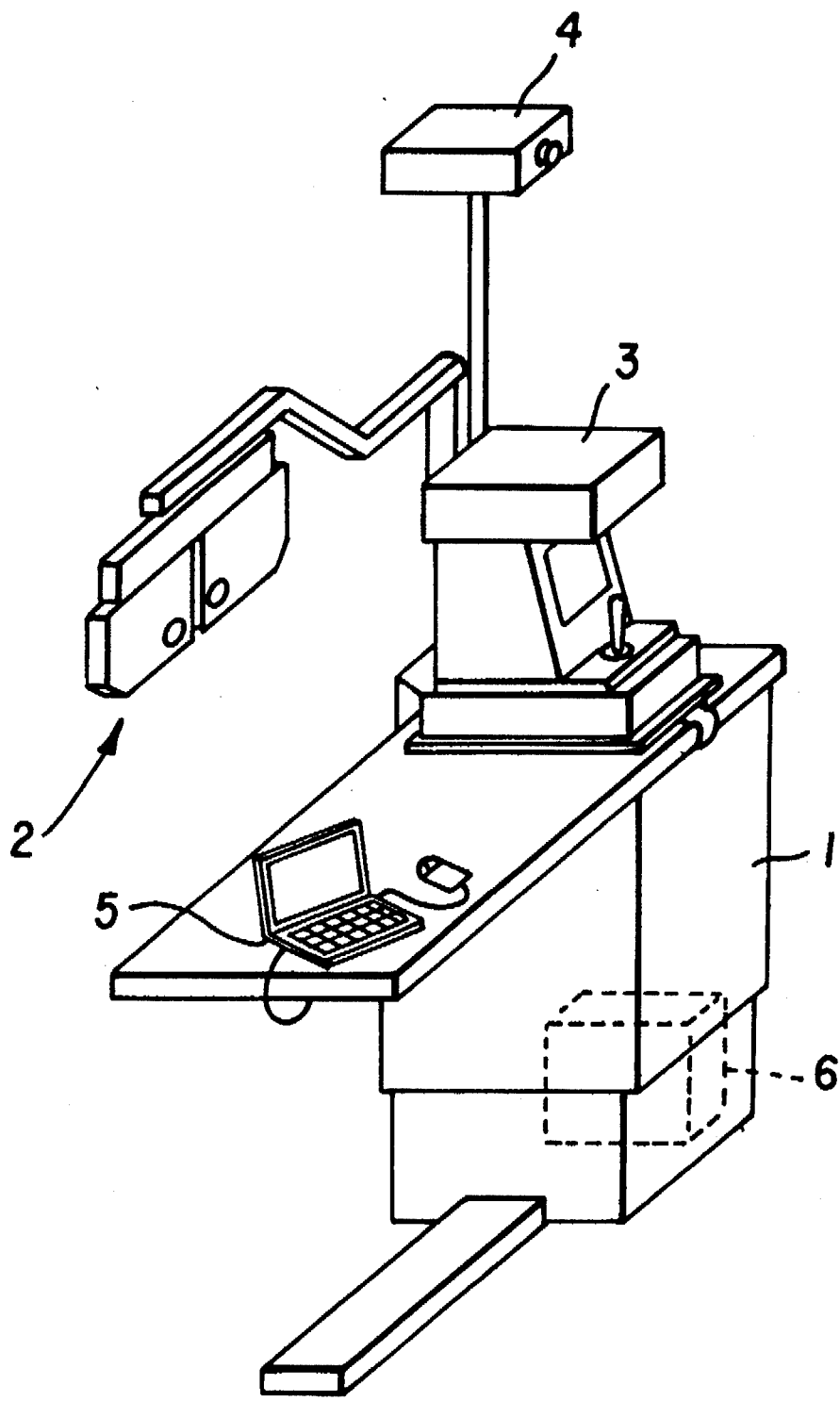
FIG. 1 is an external view showing a schematic configuration of an ophthalmic apparatus according to an embodiment/of the present invention.

One embodiment of the present invention will hereinafter be described with reference to the accompanying drawings. FIG. 1 is an external view showing a schematic configuration of an ophthalmic apparatus according to the embodiment of the present invention.

The ophthalmic apparatus according to the present embodiment roughly comprises an optometry table 1 placed between a person to be examined and an examiner, a subjective refractive power measuring device 2 for placing various optical elements in left and right ophthalmic windows by electromotive switching, an objective refractive power measuring device 3 mounted on a movable tray and slidable on the optometry table 1, a projection type object indicating device 4 for presenting a testing object, a controller 5 for operating the subjective refractive power measuring device 2 and the projection type object indicating device 4 and inputting an optometry program, and a relay unit 6 for performing a communication relay between the respective devices.

Configurations of Respective Components (Controller)

Figure 2:
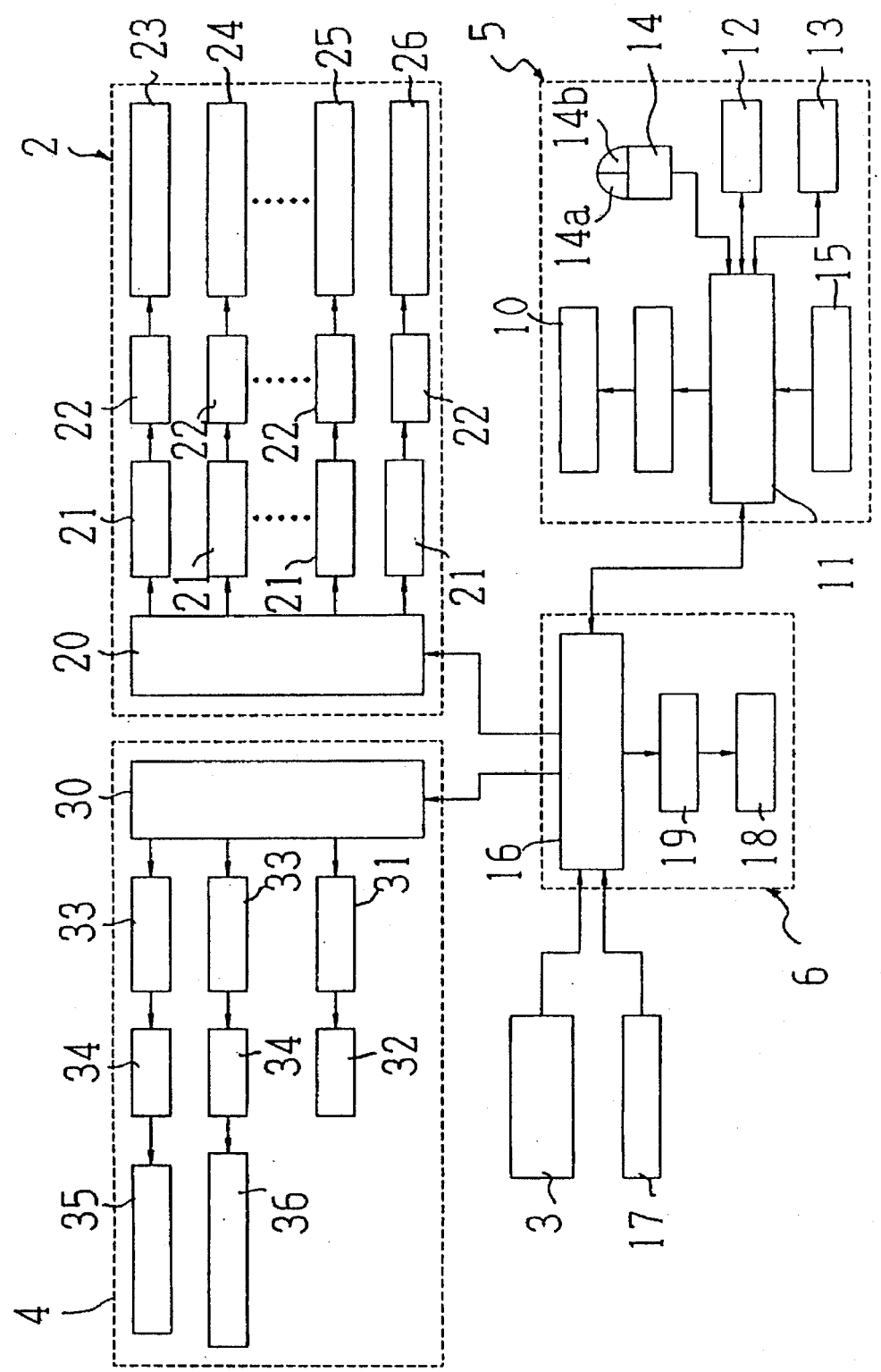
FIG. 2 is a block diagram for explaining a control system of the ophthalmic apparatus shown in FIG. 1.

FIG. 2 is a block diagram for describing a control system of the ophthalmic apparatus. Reference numeral 10 indicates a display composed of an LCD or the like. The display 10 displays various screens such as optometry information by switching and displays a plurality of screens so as to overlap each other. Reference numeral 11 indicates a microcomputer circuit, which controls the entire controller 5 and the display 10 and sends input command and program signals to the respective devices. A memory 12 for storing therein control programs such as an optometry operation screen and an optometry program input screen to be displayed on the display 10 and a memory 13 for writing and storing a plurality of optometry programs are electrically connected to the microcomputer circuit 11.

Reference numeral 14 indicates a mouse which functions as an input means for inputting a command using a pointer displayed on the display 10. The mouse 14 has two click switches 14a and 14b provided on the left and right sides thereof. Reference numeral 15 indicates a keyboard used to input characters and the like. The mouse 14 and the keyboard 15 are also electrically connected to the microcomputer circuit 11.

Incidentally, the controller 5 may be configured specifically as a means for controlling the operation of the ophthalmic apparatus and a means for inputting the optometry program. As an alternative, however, a commercially available notebook personal computer with a window display function incorporated therein may be used.

(Relay Unit)

A signal output from the microcomputer circuit 11 is input to a microcomputer circuit 18 of a relay unit 6. In response to the signal input to the microcomputer circuit 16, the microcomputer circuit 16 sends a signal about a subjective refractive power to the subjective refractive power measuring device 2 and transmits a signal about an object to the projection type object indicating device 4. Also connected to the microcomputer circuit 16 are the objective refractive power measuring device 3 and a lens meter 17. The microcomputer circuit 16 stores therein measured data sent from the two and thereafter transfers a specified measured data to the microcomputer circuit 11 when a read command signal is input to the microcomputer circuit 16 from the microcomputer circuit 11 on the controller 5 side.

Reference numeral 18 indicates a printer for outputting examined data as prints. Reference numeral 19 indicates a circuit for driving the printer 18.

(Subjective Refractive Power Measuring Device)

Reference numeral 20 indicates a microcomputer circuit for controlling the subjective refractive power measuring device 2. The microcomputer circuit 20, which has received the signal about the subjective refractive power from the microcomputer circuit 16, drives one of motors 22 through its corresponding drive circuit 21 to rotate a minor spherical disc 23, a major spherical disc 24, an auxiliary lens disc 25, a cross cylinder disc 26, etc. so as to place a predetermined optical system in a corresponding inspection window.

(Projection Type Object Indicating Device)

Reference numeral 30 indicates a microcomputer circuit fop controlling the projection type object indicating device 4. The microcomputer circuit 30 supplied with a signal about an object from the microcomputer circuit 16 turns on a lamp 32 through a drive circuit 31 and drives motors 34 through drive circuits 33 so as to rotate an object disc 35 with an object drawn thereon and a mask disc 36, thereby projecting a predetermined inspection object onto an unillustrated screen placed in front of eyes to be examined.

The optometry operation of the ophthalmic apparatus having the aforementioned construction will now be described. Although various ones are considered as procedures for implementing subjective optometry, characteristic portions of the present invention will be described herein.

Figure 3:
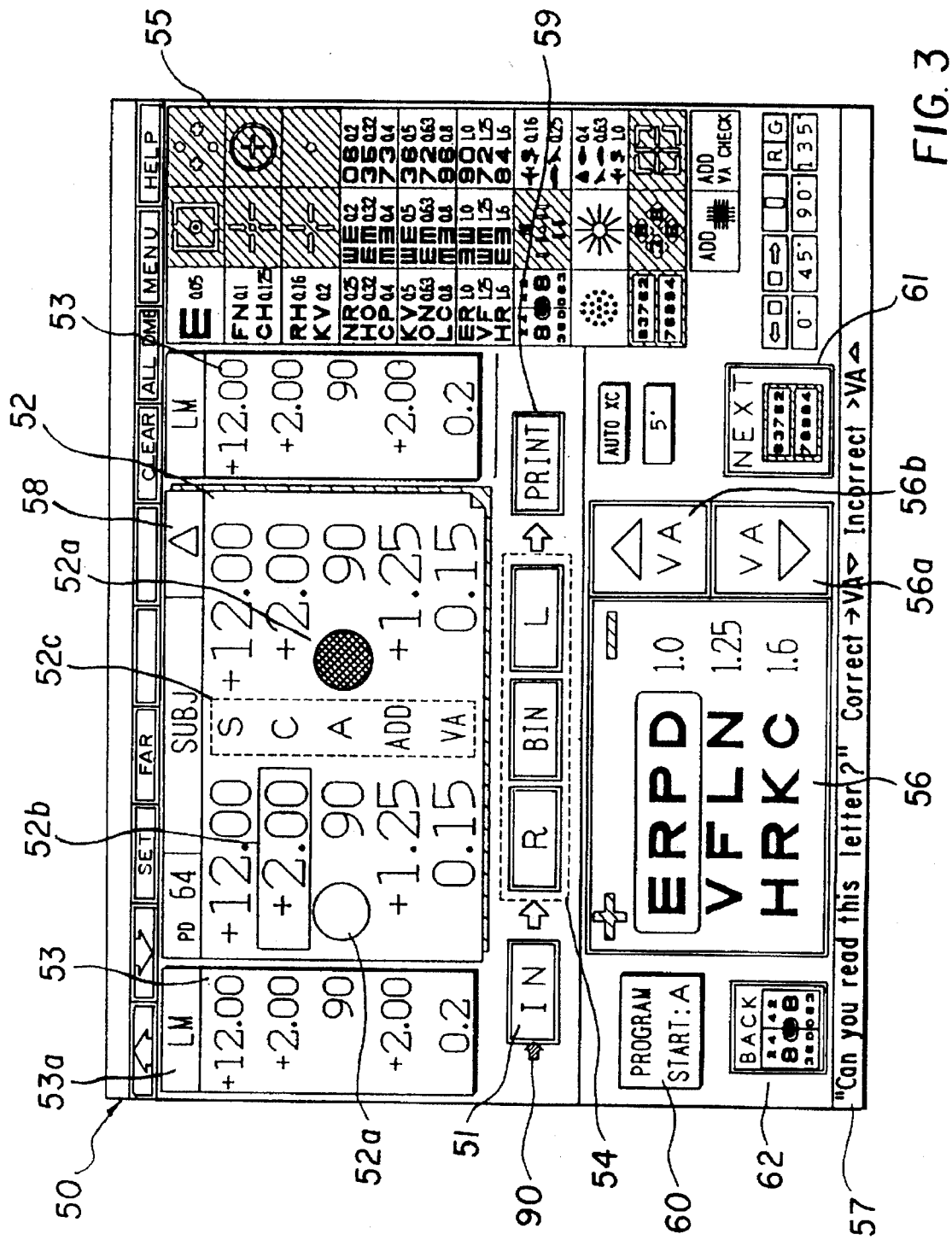
FIG. 3 is a view showing one example of an optometry operation screen displayed on a display.

FIG. 3 is a view showing one example of an optometry operation screen 50 displayed on the display 10. The optometry operation is carried out in the following manner. Namely, a pointer 90 is shifted to a displayed portion on the optometry operation screen 50 with the mouse 14, after which the left click switch 14a is pressed to specify or designate an input. When it is desired to change a numeric value such as a measured value, the pointer 90 is placed in a predetermined position and thereafter the left and right click switches 14a and 14b are pressed to change an input.

When previous spectacle data output from the lens meter 17 and objective value data output from the subjective refractive power measuring device 2 are stored in the microcomputer circuit 16 prior to the subjective optometry, these data are read into a memory provided within the microcomputer circuit 11. It is convenient to the subjective optometry if these data can be utilized for reference purposes upon determination of a subjective value.

Figure 4:
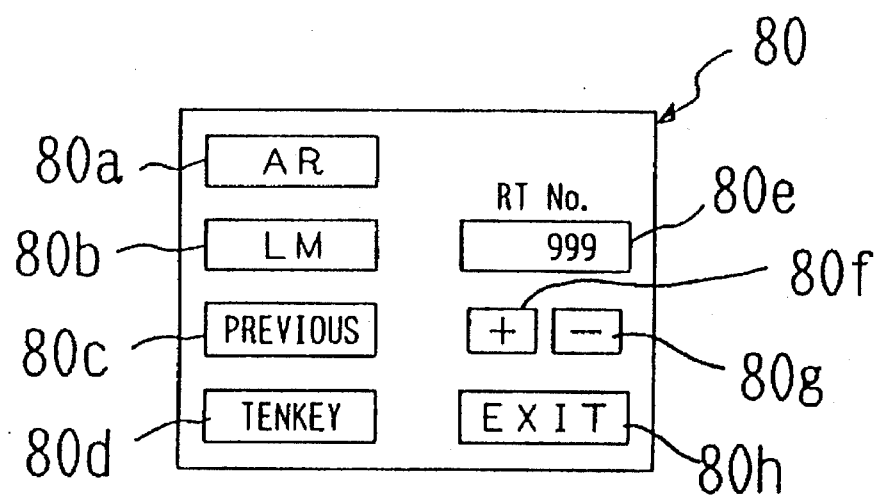
FIGS. 4(a) and 4(b) are views for describing screens displayed on the display.

When the previous spectacle data and the objective value data are read into the memory provided within the microcomputer circuit 11, the pointer 90 is first placed in an input key 51 and the left click switch 14a of the mouse 14 is pressed to designate or point a key (this operation will hereinafter be called "pointer designation"). When the input key 51 is pointer-designated, a data input list screen 80 shown in FIG. 4(a) is displayed on the optometry operation screen 50. When an LM key 80b displayed on the data input list screen 80 is pointer-designated, previous spectacle data about the latest patient number displayed on a patient number column 80e is read. Further, when an AR key 80a is pointed out, objective value data is read. Thereafter, the data input list screen 80 is closed. When it is desired to change a patient number corresponding to data to be read, a "+" key 80I or a "−" key 80g is pointer-designated to change the patient number on the displayed data input list screen 80. This change can be made even by a tenkey screen (refer to FIG. 4(b)) whose display is opened on the right side of the optometry operation screen 50 by pointer-designating a TENKEY 80d. Incidentally, a PREVIOUS key 80c on the data input list screen 80 is used when the whole optometry data about the immediately preceding person, which has been stored in the memory provided within the microcomputer circuit 11, is read out again.

Numeric data are respectively displayed on a main display portion 52 for displaying measured values or the like and reference data displays 53 located on both sides of the main display portion 52. Further, a predetermined optical system is placed in each inspection window of the subjective refractive power measuring device 2. An unillustrated selection screen can be opened by pointer-designating a data name display portion 53a so that a display can be changed under the selective operation on the selection screen. Thus, the examiner can examine the eyes while referring to various data.

An inspected eye of a person to be examined is pointer-designated with an inspection eye selection key group 54. When "R" is selected, a occuder corresponding to a kind of auxiliary lens is placed in the left inspection window of the subjective refractive power measuring device 2 so that the right eye can be examined. The types of auxiliary lenses placed in the left and right inspection windows of the subjective refractive power measuring device 2 is displayed on the main display portion 52 by graphic patterns 52a.

A desired object to be presented to the person to be examined is pointer-designated from a pattern-displayed object key group 55 displayed on the right side of the operation screen 50. The microcomputer circuit 11 sends a signal about the instructed or designated object to the object indicating device 4 through the relay unit 6 so that the object indicating device 4 presents the pointed object. Further, the microcomputer circuit 11 graphically displays the presented object on a numeric value switching area 56, based on the selected object signal. A screen example shown in FIG. 3 shows that a visual value object has been selected and pointed out. When the visual value object is selected, lateral or side mask keys 56a and 56b for shifting a side mask in upward and downward directions are displayed on the right side of the numeric value switching area 56. When the side mask keys 56a and 56b are pointer-designated, the object indicating device 4 applies a presentation mask on the same visual value alone.

When the object is selected, comments indicative of the contents to be asked of the person to be examined and the contents of operation are displayed on a comment display portion 57. The contents of predetermined comments associated with each object have been stored in the memory 12 in advance. The microcomputer circuit 11 reads and displays the corresponding contents of comments, based on the selected object signal. The display of the comments makes it possible to be of help or assistance to an examiner or the like who has little knowledge about the optometry upon optometry.

Further, the microcomputer circuit 11 displays a measuring item to be adjusted on the main display portion 52 in the form of a frame display 52b in response to the instructed object signal. This display is also carried out based on the object. In the case of a visual value object, for example, a spherical degree (S) can be numerically changed. The change of the numerical value of each item to be measured can be done by the following two ways.

According to one of the two ways, the pointer 90 is placed within a frame of the frame display 52b. Next, the left click switch 14a of the mouse 14 is pressed to increase the numeric value at a predetermined step and the right click switch 14b thereof is pressed to decrease it.

According to the other thereof, the pointer 90 is placed within the numeric value switching area 56. Next, the left click switch 14a and right click switch 14b of the mouse 14 can be driven to change the numeric value in the same manner as described above.

When it is desired to change the measuring item, a numerically-displayed portion of the main display portion 52 is pointer-designated to move the frame display 52b so that the item can be changed. Further, when one of measuring item symbols (S, C, A, ADD and VA) of a measuring item symbol area 52c is pointer-designated, a binocular visual acuity test can be selected.

When it is desired to change numerical values of both eyes, the pointer 90 is placed in the corresponding measuring item symbol of the measuring item symbol area 52c and the left and right click switches 14a and 14b of the mouse 14 are driven to increase or decrease the numerical values thereof. Alternatively, the numeric values can be also changed by placing the pointer 90 within the numeric value switching area 56.

Figure 5A:
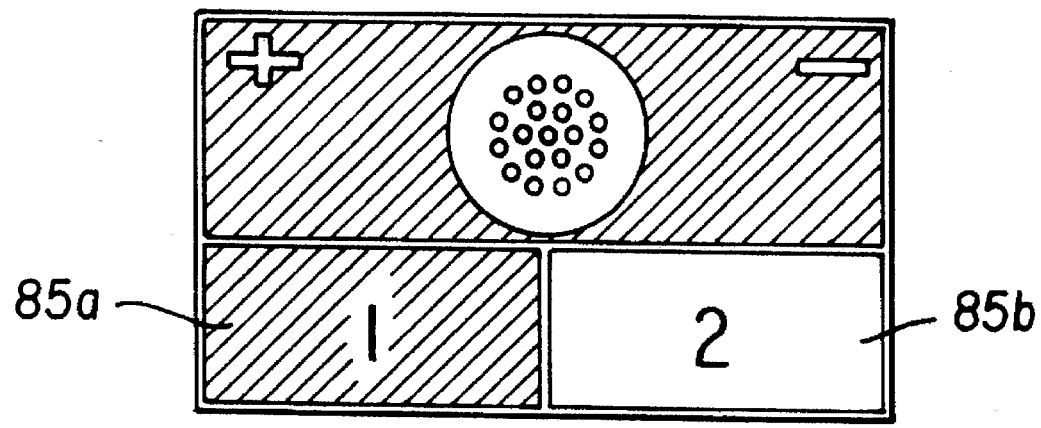
FIGS. 5(a) and 5(b) are views for explaining screens displayed on the display.
Figure 5B:
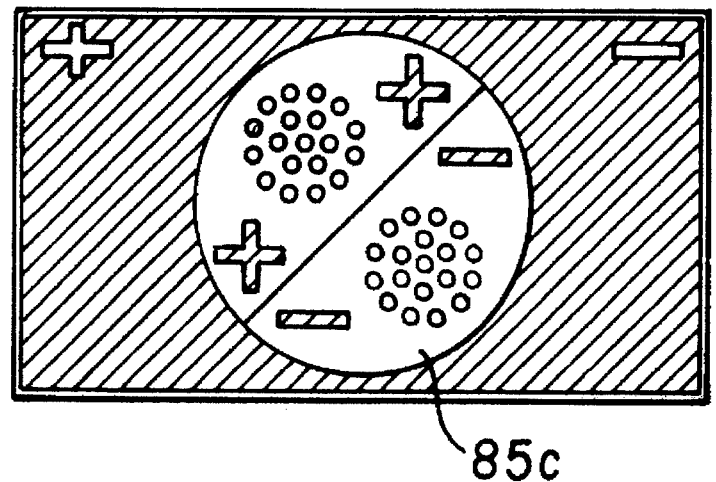

When a dot chart is selected to perform an astigmatic axis inspection and an astigmatic degree inspection in accordance with an optometry procedure, a normal cross cylinder mode or an auto cross cylinder mode is set (the normal cross cylinder mode or the auto cross cylinder mode will be set in advance on an unillustrated setting screen) and graphic patterns at either mode are displayed on the numeric value switching area 56. FIG. 5(a) shows a graphic pattern example displayed in the normal cross cylinder mode. When a "1" key 85a and a "2" key 85b are pointer-designated (a pointer-designated one is reverse-displayed), a CROSS cylinder is reversed and the pointer 90 is moved to an upper portion from an area of the key 85a or 85b, so that a numeric value for an item to be measured can be changed under the operations of the left and right click switches 14a and 14b. FIG. 5(b) illustrates a pattern example displayed in the auto cross cylinder mode. Since a pattern display 85c varies according to a changed axial angle in the auto cross cylinder mode, this display makes it easy to ask a question of an examined person as to which letter is clearer and to understand the click operation of the mouse 14, for changing the numeric value.

Figure 6A:
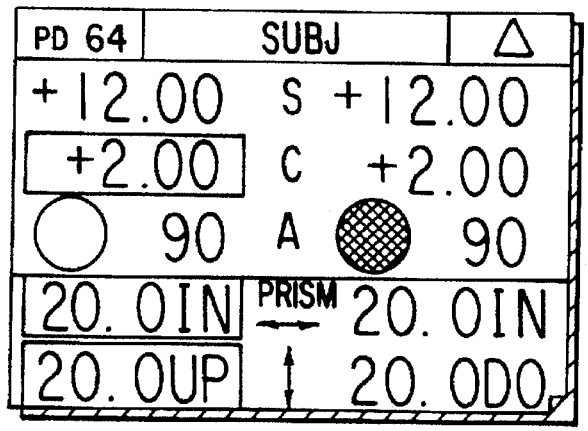
FIGS. 6(a) and 6(b) are views for describing screens displayed on the display.
Figure 6B:
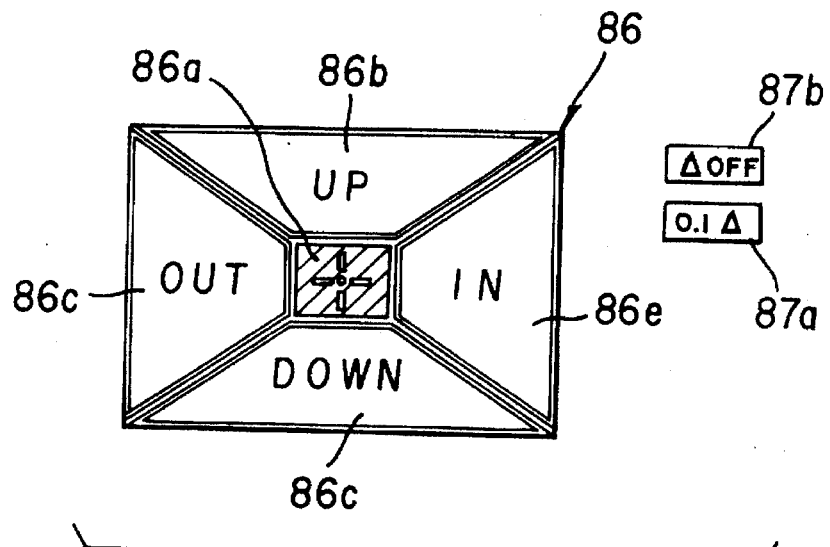

When a prism adjustment is performed for a phoria test or the like, the presented object is selected by pointer designation. Thereafter, a prism key 58 located at the right upper portion of the main display portion 52 is specified or designated by clicking. In doing so, a lower display of the main display portion 52 is changed to a prism measuring item display shown in FIG. 6(a). Further, the display of the numeric value switching area 56 is changed to a screen display 86 shown in FIG. 6(b) having an object graphic pattern 86a and prism value change keys 86b through 86e with operation descriptions (FIG. 6(b) shows a display example in a right-eye change mode and a binocular change mode, and "OUT" and "IN" are reversely displayed in the case of a left-eye change mode). A prism value in the direction that is desired to be changed, can be changed at a predetermined step by pointer-designating the prism value change keys 86b through 86e. A change step can be also switched by pointer-designating reference numeral 87a displayed on the right upper portion of the screen display 86. Reference numeral 87b is used when a prism placed in each inspection window is inserted into and removed from the inspection window.

After the optometry has been completed and the result of measurements has been obtained, a print key 59 is pointer-designated to output prints from the printer 18.

The optometry to be performed in accordance with the pre-set program optometry will now be described briefly.

In the optometry operation screen 50, reference numeral 60 indicates a program start key which doubles as a program name display. In the present embodiment, a program A is illustrated. A plurality of optometry programs can be stored in the memory 13. Each optometry program can be input through an unillustrated program input screen.

Figure 7:
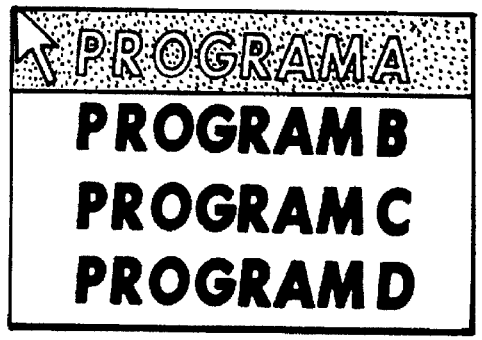
FIG. 7 is a view illustrating a displayed example of a program name list displayed on the display.

When an expected or desired program is selected from the plurality of optometry programs stored in the memory 13, the following operation is executed. When the pointer 90 is placed in the program start key 60 with the mouse 14 and then shifted to the outside of the display while the left click switch 14a is being pressed, and the left click switch 14a is released from pressing, a program name list (refer to FIG. 7) is opened. By pointer-designating a desired program name in the program name list, the display of the program start key 60 is changed to the selected program name.

The program optometry is executed as follows. When the program start key 60 is pointer-designated, the microcomputer circuit 11 reads out the corresponding optometry program stored in the memory 13. Further, the microcomputer circuit 11 allows the object indicating device 4 to present an object (object masked when the mask is necessary) based on the contents of the program and causes the subjective refractive power measuring device 2 to place an auxiliary lens in its corresponding inspection window. Furthermore, the microcomputer circuit 11 allows the display 10 to indicate respective displays.

When the numeric value for each measuring item indicated by the frame display 52b of the main display portion 52 is changed at each optometry step, the pointer 90 is placed within the numeric value switching area 56 or the frame display 52b with the mouse 14 and the left and right click switches 14a and 14b are pressed to change the numeric value in the same manner as the aforementioned optometry operation.

When the inspecting items step proceeds to the next inspecting items step under the optometry program, a program forward key 61 in which the contents of the next inspecting items are displayed in the form of an object pattern, is pointer-designated. When the inspecting items step is returned to the immediately preceding inspecting items step which has been already executed, a program back key 62 displayed in the form of an object pattern is pointer-designated.

Having now fully described the invention, it will be apparent to those skilled in the art that many changes and modifications can be made without departing from the spirit or scope of the invention as set forth herein.

What is claimed is:

1. An ophthalmic apparatus for inspecting visual functions of eyes to be examined, comprising:

an optical unit having ophthalmic windows, for respectively placing optical elements in the ophthalmic windows by switching;

an object indicating unit for presenting an object to each eye to be examined;

display means having an operation screen for operating said object indicating unit and said optical unit;

program storing means for storing therein programs for controlling said display means, said programs having a common numeric value switching area for effecting the switching values for respective measuring items such as a spherical degree, an astigmatic degree and an astigmatic axis, and displaying an operation screen displaying an object presented by said object indicating unit and an input screen inputting reference data for inspecting the eyes to be examined within said numeric value switching area;

input means for inputting an operation command through the use of the operation screen of said display means; and program executing means for executing the programs in accordance with the input operation command.

2. An ophthalmic apparatus according to claim 1, wherein the programs stored in said program storing means further include a program for displaying a prism-value changing operation screen having both change keys indicative of keys for changing a prism value and operation instructions indicative of the way of operating the change keys.

3. An ophthalmic apparatus according to claim 1, wherein the programs stored in said program storing means further displays a numeric value display portion for displaying the numeric values for the respective inspecting items such as the spherical degree, the astigmatic degree and the astigmatic axis, and an operation screen having a monocular change area for changing a monocular numeric value and a binocular change area for changing binocular numeric values, said both areas being included in the numeric value display portion.

4. An ophthalmic apparatus according to claim 1, wherein said reference data input screen has a first input screen for making switching to an input mode and a second input screen for selecting the type of reference data displayed subsequently after the switching to the input mode by the first input screen.

5. An ophthalmic apparatus according to claim 1, wherein the programs stored in said program storing means include a program for invoking the input reference data and providing instructions for placing a lens corresponding to the reference data in a corresponding ophthalmic window of said optical unit.

6. An ophthalmic apparatus according to claim 5, wherein the programs stored in said program storing means include a program for displaying the reference data within the operation screen.

7. An ophthalmic apparatus according to claim 1, wherein the programs stored in said program storing means further include an optometry program for defining an optometry procedure and a program for displaying the type of measuring items before and after steps of the present measuring items within the operation screen.

8. An ophthalmic apparatus according to claim 1, wherein said input means is an input mouse, and the programs stored in said program storing means include a plurality of optometry programs for defining optometry procedures and display optometry program selection screens by shifting a pointer to a program start key on the operation screen with the input mouse and performing a predetermined click operation of the input mouse.

9. An ophthalmic apparatus for inspecting visual functions of eyes to be examined, comprising:

an optical unit having ophthalmic windows, for respectively placing optical elements in the ophthalmic windows by switching;

an object indicating unit for presenting an object to each eye to be examined;

display means having an operation screen for operating said object indicating unit and the optical elements placed in said optical unit;

program storing means for storing therein programs for controlling said display means, said programs displaying an operation screen having numeric value display portions for respectively displaying numeric values for respective measuring items such as a spherical degree, an astigmatic degree and an astigmatic axis, and a monocular change area for changing a monocular numeric value and a binocular change area for changing binocular numeric values, said both areas being included in said each numeric value display portion;

input means for inputting an operation command through the operation screen of said display means; and program executing means for executing the programs in accordance with the input operation command.

10. An ophthalmic apparatus according to claim 9, wherein said input means is an input mouse which places a pointer under the input mouse in the monocular change area where each monocular numeric value is displayed.

* * * * *